(12) United States Patent
Loescher et al.

(10) Patent No.: US 8,853,483 B2
(45) Date of Patent: Oct. 7, 2014

(54) OLIGOMERIZATION PROCESS

(75) Inventors: Mitchell E. Loescher, Houston, TX (US); Turi Odegard, Houston, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 88 days.

(21) Appl. No.: 12/326,488

(22) Filed: Dec. 2, 2008

(65) Prior Publication Data

US 2010/0137668 A1   Jun. 3, 2010

(51) Int. Cl.
*C07C 2/28* (2006.01)
*C07C 29/04* (2006.01)
*C10L 1/02* (2006.01)
*C10G 69/12* (2006.01)
*C10G 50/00* (2006.01)
*C07C 41/06* (2006.01)

(52) U.S. Cl.
CPC . *C07C 2/28* (2013.01); *C07C 29/04* (2013.01); *C10L 1/02* (2013.01); *C10L 1/026* (2013.01); *C10G 69/126* (2013.01); *C07C 2531/08* (2013.01); *C10L 1/023* (2013.01); *C10G 50/00* (2013.01); *C07C 41/06* (2013.01)
USPC ........... 585/515; 585/510; 585/520; 585/526; 585/527; 585/529

(58) Field of Classification Search
CPC ........ C07C 2/28; C07C 2531/08; C07C 29/04
USPC .................. 585/510, 520, 526, 529, 515, 527
See application file for complete search history.

(56) References Cited

U.S. PATENT DOCUMENTS

| | | | |
|---|---|---|---|
| 2,135,117 A | * | 11/1938 | Stevens et al. ................ 585/526 |
| 4,242,530 A | | 12/1980 | Smith, Jr. |
| 4,313,016 A | | 1/1982 | Manning |
| 4,375,576 A | | 3/1983 | Smith, Jr. |
| 4,540,839 A | | 9/1985 | Keyworth et al. |
| 4,695,664 A | | 9/1987 | Whittle |
| 4,956,514 A | | 9/1990 | Chu |
| 5,003,124 A | | 3/1991 | Smith, Jr. et al. |
| 5,510,555 A | | 4/1996 | Brunelli et al. |
| 5,723,687 A | * | 3/1998 | Marchionna et al. ......... 568/697 |
| 6,011,191 A | * | 1/2000 | Di Girolamo et al. ........ 585/514 |
| 6,143,942 A | | 11/2000 | Verrelst et al. |

(Continued)

OTHER PUBLICATIONS

CS ChemProp calculation (boiling points estimated by CS ChemProp in ChemDraw Ultra, 12.0, copyright CambridgeSoft, Inc., 2010).*

(Continued)

*Primary Examiner* — In Suk Bullock
*Assistant Examiner* — Bradley Etherton
(74) *Attorney, Agent, or Firm* — Osha Liang LLP

(57) ABSTRACT

A process for oligomerizing isoolefins, the process including: feeding an isoolefin to an oligomerization reaction zone; feeding an oxygen-containing reaction moderator to the oligomerization reaction zone; concurrently in the oligomerization reaction zone: contacting the isoolefin with an oligomerization catalyst to convert at least a portion of the isoolefin to oligomers comprising dimers and trimers of the isoolefin; reacting a portion of the moderator with a portion of at least one of the isoolefin and the oligomers to form an oxygenated oligomerization byproduct; recovering an effluent from the oligomerization reaction zone comprising the oligomers and the oxygenated oligomerization byproduct; fractionating at least a portion of the effluent to recover a fraction comprising the oxygenated oligomerization byproduct and the trimers and a fraction comprising the dimers.

21 Claims, 2 Drawing Sheets

(56) References Cited

U.S. PATENT DOCUMENTS

| | | | |
|---|---|---|---|
| 6,335,473 | B1 | 1/2002 | Bakshi et al. |
| 6,376,731 | B1 * | 4/2002 | Evans et al. ................... 585/510 |
| 6,501,001 | B2 | 12/2002 | Commereuc et al. |
| 6,613,108 | B1 * | 9/2003 | Aittamaa et al. ................. 44/449 |
| 6,936,742 | B2 * | 8/2005 | Smith, Jr. ...................... 585/327 |
| 7,038,101 | B2 * | 5/2006 | Nurminen et al. ............ 585/504 |
| 7,145,049 | B2 | 12/2006 | Loescher et al. |
| 7,601,880 | B2 * | 10/2009 | Pyhalahti ...................... 585/733 |
| 2004/0097773 | A1 | 5/2004 | Beckmann et al. |
| 2006/0122444 | A1 | 6/2006 | Peters et al. |
| 2006/0287565 | A1 * | 12/2006 | Du Toit ......................... 585/533 |
| 2008/0242909 | A1 * | 10/2008 | Di Girolamo et al. ........ 585/639 |

OTHER PUBLICATIONS

DeGarmo, et al., "Consider Reactive Distillation" in Chemical Engineering Progress, p. 43-50, Mar. 1992.*

International Search Report and Written Opinion issued May 24, 2010 in corresponding International Application No. PCT/US2009/063418 (7 pages).

Second Office Action (with translation) issued Oct. 8, 2013 in corresponding Korean application No. 10-2011-7013538 (11 pages).

Office Action (with translation) issued Mar. 26, 2013 in corresponding Korean application No. 10-2011-7013538 (7 pages).

* cited by examiner

OLIGOMERIZATION PROCESS

BACKGROUND OF DISCLOSURE

1. Field of the Disclosure

Embodiments disclosed herein relate generally to oligomerization of isoolefins. In another aspect, embodiments disclosed herein relate to oligomerization of isoolefins using an oxygen-containing reaction moderator.

2. Background

Isobutene is commercially significant in many applications. For example, isobutene is one of the comonomers in butyl rubber. Isobutene can also be oligomerized to produce compounds that can be used as chemical feedstock for further reacting or in gasoline blending. Diisobutene, the isobutene dimer, is of particular commercial value in several applications. For example, diisobutene can be used as an alkylation reaction feedstock or as an intermediate in the preparation of detergents. Diisobutene can also be hydrogenated to pure isooctane (2,2,4 tri-methyl pentane) that is highly preferred in gasoline blending.

Isoolefin oligomerization is a catalytic reaction that uses an acid catalyst. For example, oligomerization of isoolefins has been disclosed in U.S. Pat. Nos. 4,242,530, 4,375,576, 5,003,124, and 7,145,049, among others.

When an isoolefin, in particular isobutene, is oligomerized, it is desired to limit the progress of the oligomerization reaction to the dimer stage. High dimer selectivity may be achieved by adding suitable moderator to the reaction mixture, for example, a certain polar component. Typically, oxygenates, such as water, primary, secondary and tertiary alcohols and ethers, are used as the moderator. Use of MTBE as a reaction moderator, for example, is disclosed in U.S. Pat. No. 4,375,576.

The presence of oxygenates makes certain side reactions possible. Such side reactions between the moderator and the isobutene and/or its oligomers leads to formation of heavy oxygenates. Representative moderator side reactions are as follows:

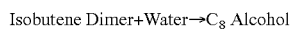

Isobutene Dimer+Water→$C_8$ Alcohol

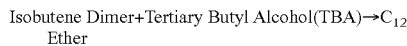

Isobutene Dimer+Tertiary Butyl Alcohol(TBA)→$C_{12}$ Ether

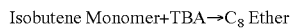

Isobutene Monomer+TBA→$C_8$ Ether

Isobutene Dimer+Methanol→$C_9$ Ether

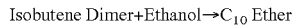

Isobutene Dimer+Ethanol→$C_{10}$ Ether

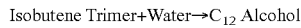

Isobutene Trimer+Water→$C_{12}$ Alcohol

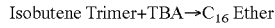

Isobutene Trimer+TBA→$C_{16}$ Ether

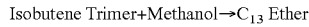

Isobutene Trimer+Methanol→$C_{13}$ Ether

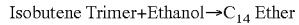

Isobutene Trimer+Ethanol→$C_{14}$ Ether

The oxygenated byproducts contained in the selectively dimerized isobutene must be substantially removed prior to further use of the dimers, for example, in alkylation and gasoline blending.

The selectively dimerized isobutene, for example, can be used in an alkylation reaction to produce various derivatives. Alkylation is typically a catalytic process, the efficiency of which depends on the catalyst life and performance. The presence of certain feed impurities, such as oxygenates, can poison the alkylation catalyst, thus adversely affecting its performance and increasing the frequency of expensive catalyst change-outs. Accordingly, oxygenates are not desirable in an alkylation feedstock.

As another example, the selectively dimerized isobutene may also be used in gasoline blending. As above, dimerization products are high value gasoline additives due to their high octane rating. However, the presence of oxygenates in the gasoline fuel can create various environmental, safety, and combustion performance problems due to the nature and properties of certain oxygenates, for example, certain alcohols and ethers. Even though certain ethers can actually improve gasoline combustion, the negative publicity around methyl tertiary butyl ether (MTBE) and other ethers has created a problem for gasoline producers, prompting removal of oxygenates from fuel.

Hydrogenation is typically used to remove oxygenates from the selectively dimerized isobutene. However, hydrogenation requires considerable hydrogen consumption that can add significant operating costs. Also, hydrogenation can often lead to undesirable saturation of olefins, thus resulting in loss of the octane rating and the reduced market value of the selectively dimerized isobutene.

Accordingly, there exists a need for improved methods for producing oligomers of isoolefins.

SUMMARY OF THE DISCLOSURE

In one aspect, embodiments disclosed herein relate to a process for oligomerizing isoolefins, the process including: feeding an isoolefin to an oligomerization reaction zone; feeding an oxygen-containing reaction moderator to the oligomerization reaction zone; concurrently in the oligomerization reaction zone: contacting the isoolefin with an oligomerization catalyst to convert at least a portion of the isoolefin to oligomers comprising dimers and trimers of the isoolefin; reacting a portion of the moderator with a portion of at least one of the isoolefin and the oligomers to form an oxygenated oligomerization byproduct; recovering an effluent from the oligomerization reaction zone comprising the oligomers and the oxygenated oligomerization byproduct; fractionating at least a portion of the effluent to recover a fraction comprising the oxygenated oligomerization byproduct and the trimers and a fraction comprising the dimers.

In another aspect, embodiments disclosed herein relate to a process for oligomerizing isobutene, the process including: feeding isobutene to an oligomerization reaction zone; feeding an oxygen-containing reaction moderator to the oligomerization reaction zone; concurrently in the oligomerization reaction zone: contacting the isobutene with an oligomerization catalyst to convert at least a portion of the isobutene to oligomers comprising dimers and trimers of isobutene; reacting a portion of the moderator with a portion of at least one of the isobutene and the oligomers to form an oxygenated oligomerization byproduct; recovering an effluent from the oligomerization reaction zone comprising the oligomers and the oxygenated oligomerization byproduct; fractionating at least a portion of the effluent to recover a fraction comprising the oxygenated oligomerization byproduct and the trimers and a fraction comprising the isobutene dimers.

Other aspects and advantages will be apparent from the following description and the appended claims.

DETAILED DESCRIPTION

Figure 1:
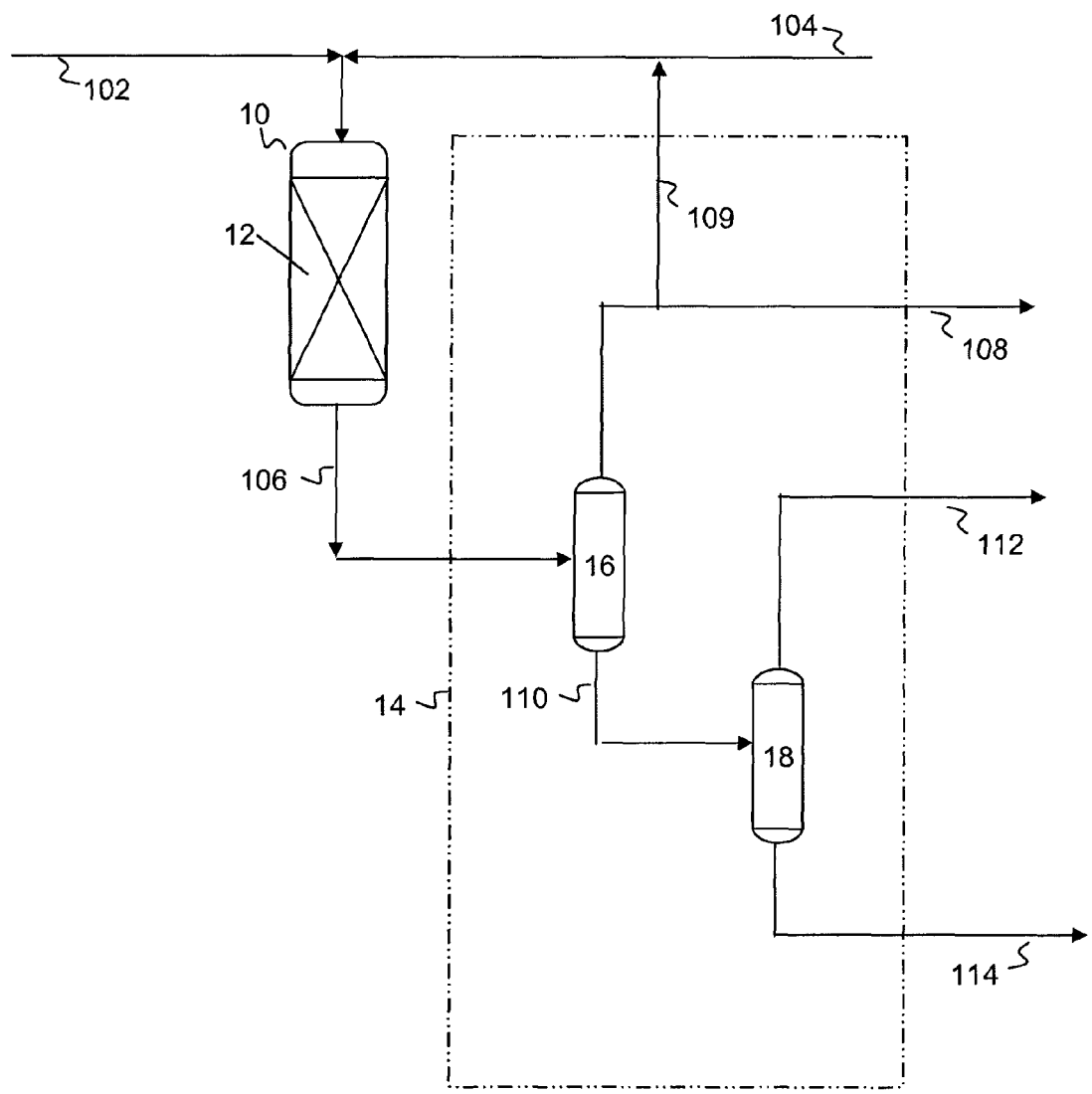
FIG. 1 is a simplified flow diagram of an oligomerization process according to embodiments disclosed herein.

In one aspect, embodiments disclosed herein relate generally to oligomerization of isoolefins. In another aspect, embodiments disclosed herein relate to oligomerization of isoolefins using an oxygen-containing reaction moderator.

Oligomerization may be carried out, for example, in a partial liquid phase in the presence of an acid cation resin catalyst, either in straight pass type reaction, such as that disclosed in U.S. Pat. Nos. 4,313,016, 4,540,839, 5,003,124, and 6,335,473, or in a catalytic distillation reaction where there is both a vapor and a liquid phase and a concurrent reaction/fractionation. Isoolefins that may be oligomerized may include isobutene, isopentenes (isoamylenes), and combinations thereof, which are more reactive than n-olefins, and are selectively oligomerized.

The primary oligomer products are dimers and trimers of isoolefins. For example, isobutene may be oligomerized to form a $C_8$ or $C_{12}$ tertiary olefin, isopentene may be oligomerized to form a $C_{10}$ or $C_{15}$ tertiary olefin, and mixtures of isobutene and isopentene may be reacted to form $C_8$ to $C_{15}$ tertiary olefins, among other products. $C_6$ to $C_{15}$ olefin oligomers may also be prepared from $C_3$ to $C_5$ olefins. In some embodiments, the oligomers have 8 to 16 carbon atoms and correspond to oligomers which are prepared from $C_4$ to $C_5$ olefins. The oligomerization of the tertiary olefin may also be performed when carried out on a light naphtha stream with the separation of normal olefins being easily achieved by fractionation from the heavier (higher boiling) oligomers (mainly dimers and trimers).

The oligomerization of isoolefins may be carried out in a partial liquid phase in the presence of an acid cation resin catalyst either in straight pass type reaction or in a catalytic distillation reaction where there is both a vapor and liquid phase and a concurrent reaction/fractionation. Catalysts used in oligomerization reactors may include acid resins, such as AMBERLYST 15 or related oleum derived resins and may include phosphoric acid derived catalysts, such as those known to the industry as SPA (solid phosphoric acid) catalysts.

The feed to the oligomerization reactor may include purified isoolefin streams, such as a feed stream containing, propylene, isobutane, isoamylenes, or mixtures thereof. In other embodiments, oligomerization fees may include a $C_4$-$C_5$, $C_4$ or $C_5$ light naphtha cut. When present in mixtures, the tertiary olefins, such as isobutene and isoamylenes, are more reactive than the normal olefin isomers and are preferentially oligomerized. The primary oligomerization products are dimers and trimers of the $C_3$ to $C_5$ olefins. The isoalkanes in the $C_4$ to $C_5$ light naphtha cut may include isobutane, isopentane or mixtures thereof, as a diluent in the oligomerization reactor.

Oxygen-containing moderators may be used to influence the selectivity of the oligomerization reaction to the dimer product. Oxygen-containing moderators useful in embodiments disclosed herein may include water as well as primary, secondary and tertiary alcohols and ethers. For example, the oxygen-containing moderator may include at least one of: water, tertiary butyl alcohol, methanol, methyl tertiary butyl ether, ethanol, and ethyl tertiary butyl ether.

Oligomerization reactions carried out in the presence of the oxygen-containing moderators may concurrently produce oligomers, such as dimers and trimers of the isoolefins, and various oxygen-containing byproducts due to reaction of a moderator with an isoolefin or an isoolefin oligomer, such as a dimer or trimer. For example, the oxygenated oligomerization byproducts may include $C_8$-$C_{16}$ ethers and $C_8$-$C_{12}$ alcohols.

The oligomerization reactors used in embodiments disclosed herein may include any physical devices or a combination of two or more devices. The reactors may have various internal devices for vapor-liquid separation and vapor/liquid traffic. Any type of reactor may be used to carry out the reactions described herein. The examples of reactors suitable for carrying out the reactions involving isoolefin dimerization or oligomerization reactions may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors. Multiple reactor systems useful in embodiments disclosed herein may include a series of multiple reactors or multiple reactors in parallel for the first reaction zone. A person of ordinary skill in the art would recognize that other types of reactors may also be used.

For example, straight pass oligomerization reactors may be used, such as disclosed in U.S. Pat. Nos. 4,313,016; 4,540,839; 5,003,124; and 6,335,473. The oligomerization of propylene may be carried out, for example, in tubular reactors at 330-482° F. and 1000 to 1215 psig using supported phosphoric acid (sPa), metal complexes (U.S. Pat. Nos. 5,510,555; 4,695,664 and 6,501,001) and various zeolites, especially ZSM-22, ZSM-57 (U.S. Pat. No. 6,143,942) and MCM-22 (U.S. Pat. No. 4,956,514) which has been shown to have favorable characteristics for the oligomerization of propylene at lower pressures and temperatures than the other catalysts. In such straight pass reactors, the effluent from the oligomerization reaction zone may include the oligomers, unreacted propylene and/or isoolefins, oxygen-containing reaction moderators, and oxygenated oligomerization byproducts.

As another example, the oligomerization may be carried out in a catalytic distillation type reaction, such as that disclosed in U.S. Pat. Nos. 4,242,530 or 4,375,576. During catalytic distillation, the oligomers and the oxygenated oligomerization byproducts may be fractionated from unreacted isoolefins and other light hydrocarbons. The unreacted isoolefins and other light hydrocarbons, when present, may be recovered as an overheads fraction, a fraction of which may also be used as column reflux. The oligomers and oxygenated oligomerization byproducts may be recovered as a bottoms fraction, where the bottoms fraction is herein defined as the reactor effluent from a catalytic distillation column. Depending upon the type of reaction moderator used and the conditions in the distillation column reactor, the oxygen-containing reaction moderator may be recovered with either or both the overheads fraction and the bottoms fraction.

The reaction effluent, including the oligomers and the oxygenated oligomerization byproduct, or a portion thereof, may then be fractionated to recover a fraction including the oxygenated oligomerization byproduct and the trimers and a fraction including the dimers.

When the reactor effluent further includes unreacted isoolefin and/or oxygen-containing moderator, such as from a straight-pass reactor, the reactor effluent may be fractionated to additionally recover a fraction containing the oxygen-containing moderator and/or the unreacted isoolefin, which may be recycled to the oligomerization reaction zone in some embodiments. Any separation scheme to produce three separate fractions, including a light fraction (moderator and/or unreacted isoolefin), a medium fraction (dimers), and a heavy fraction (trimers and oxygenated oligomerization byproducts), may be used.

For example, in some embodiments, the desired fractions may be obtained using a first distillation column to separate the lights fraction from the medium and heavy fractions followed by separation of the medium and heavy fractions. In other embodiments, the desired fractions may be obtained using a first distillation column to separate the heavy fraction from the light and medium fraction followed by separation of the light and medium fractions. In yet other embodiments, a single distillation column or a divided wall distillation column including a side draw may be used to provide the desired separations. One skilled in the art would recognize that other means to obtain the desired fractions can be used.

The dimer (e.g., $C_8$ olefins) fraction produced in embodiments disclosed herein may have a purity of at least 99.5 weight percent; at least 99.7 weight percent in other embodiments; and at least 99.8 weight percent in yet other embodiments. The total concentration of oxygenates in the recovered dimer fraction may be less than 500 ppm in some embodiments; less than 400 ppm in other embodiments; and less than 250 ppm in yet other embodiments.

Referring to FIG. 1, a process for oligomerizing isoolefins according to embodiments disclosed herein is illustrated. An isoolefin, such as isobutene, is fed to an oligomerization reaction zone 10 via flow line 102. An oxygen-containing moderator may be fed to dimerization reaction zone 10 via flow line 104. The isoolefin reacts in the presence of the oligomerization catalyst 12 contained in dimerization reaction zone 10 to convert a portion of the isoolefin to oligomers, including dimers and trimers. As a side reaction, the moderator may react with a portion of at least one of the isoolefin and the oligomerization products in dimerization reaction zone 10 to form an oxygenated oligomerization byproduct. Effluent, containing the oligomerization product and the oxygenated oligomerization byproducts, as well as any unreacted moderator and isoolefin, may be recovered from dimerization reaction zone 10 via flow line 106.

The reaction effluent may then be fed to separation unit 14 to separate the reaction effluent into the desired fractions. For example, the reaction effluent may be fed via flow line 106 to a first distillation column 16 to separate the moderator and unreacted isoolefin from the oligomers and the oxygenated oligomerization byproducts. The unreacted isoolefin and moderator may be recovered as an overheads fraction via flow line 108, and the oligomers and oxygenated oligomerization byproducts may be recovered via flow line 110. If desired, the moderator and unreacted isoolefin may be recycled to the oligomerization reaction zone via flow line 109.

The bottoms fraction may then be fed via flow line 110 to a second distillation column 18, where the dimers may be separated from the trimers and the oxygenated oligomerization byproducts. The dimers may be recovered as an overheads fraction from column 18 via flow line 112, and the trimers and oxygenated oligomerization byproducts may be recovered via flow line 114, where each may be used in downstream processes as described above.

Figure 2:
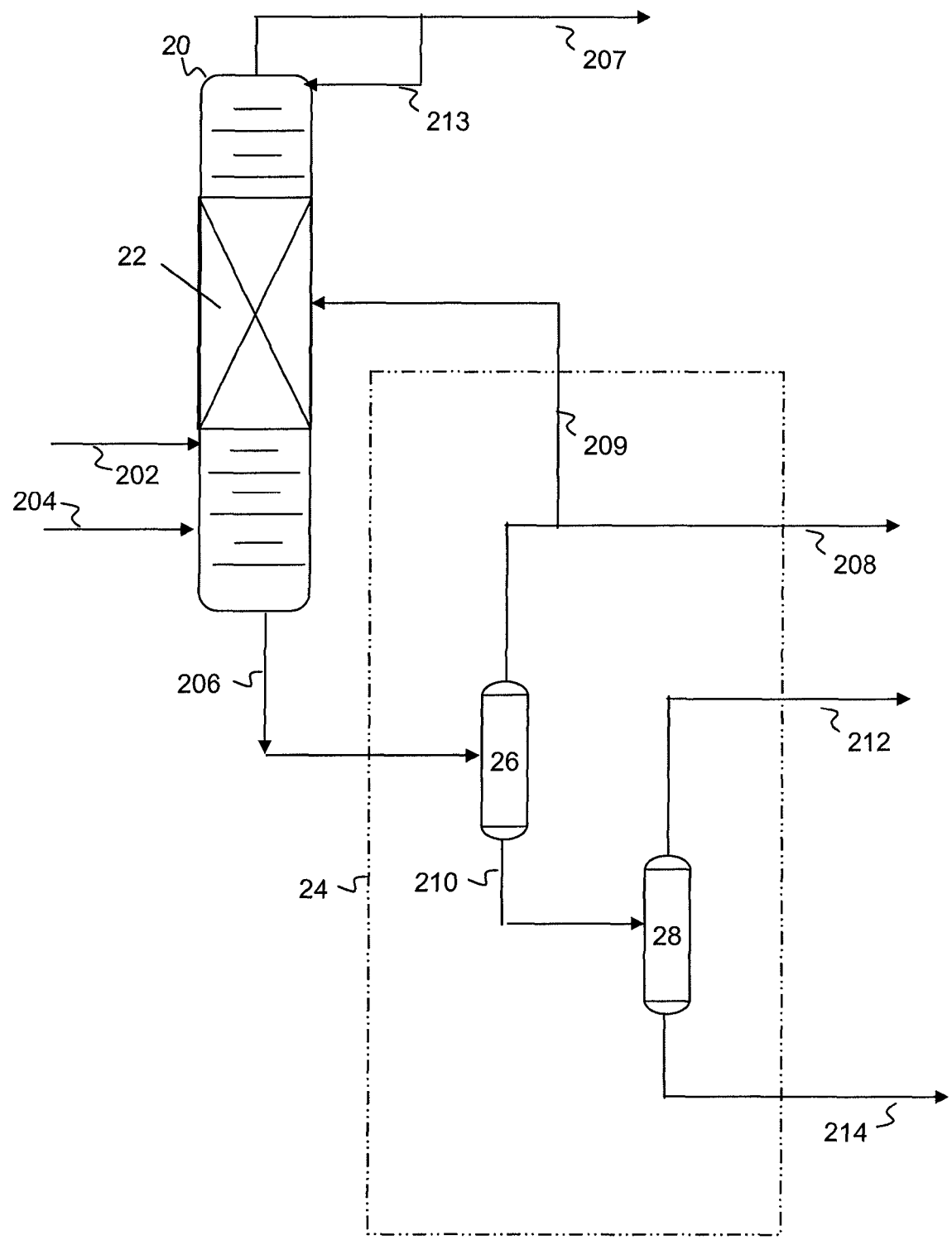
FIG. 2 is a simplified flow diagram of an oligomerization process according to embodiments disclosed herein.

Referring now to FIG. 2, a process for oligomerizing isoolefins according to embodiments disclosed herein is illustrated. An isoolefin and a moderator may be fed via flow lines 202 and 204, respectively, to a catalytic distillation column 20 containing a bed 22 of oligomerization catalyst. Concurrently in the catalytic distillation column: (a) isoolefin reacts in the presence of the oligomerization catalyst to form oligomers, including dimers and trimers; (b) at least a portion of the moderator may react with a portion of at least one of the isoolefin and the oligomers to form oxygenated oligomerization byproducts; (c) unreacted isoolefin is separated from the oligomers and oxygenated oligomerization byproducts. The unreacted isoolefin may be recovered as an overhead fraction via flow line 207, a portion of which may be used as column reflux via flow line 213. The oligomers and oxygenated oligomerization byproducts may be recovered as a bottoms fraction via flow line 206.

The bottoms fraction may then be fed to separation unit 24 to separate the reaction effluent into the desired fractions. For example, the reaction effluent, which may include unreacted moderator, may be fed via flow line 206 to a first distillation column 26 to separate the moderator and unreacted isoolefin from the oligomers and the oxygenated oligomerization byproducts. The unreacted moderator may be recovered as an overheads fraction via flow line 208, and the oligomers and oxygenated oligomerization byproducts may be recovered via flow line 210. If desired, the moderator may be recycled to the oligomerization reaction zone via flow line 209.

The bottoms fraction may then be fed via flow line 210 to a second distillation column 28, where the dimers may be separated from the trimers and the oxygenated oligomerization byproducts. The dimers may be recovered as an overheads fraction from column 28 via flow line 212, and the trimers and oxygenated oligomerization byproducts may be recovered via flow line 214, where each may be used in downstream processes as described above.

As described above, oligomerization processes disclosed herein may result in a product stream (112, 212) containing isoolefin dimers having a reduced amount of oxygenated byproducts. In some embodiments, the dimer fraction may include less than 100 ppm oxygen, by weight; less than 50 ppm oxygen, by weight, in other embodiments; and less than 25 ppm oxygen, by weight, in yet other embodiments.

The resulting dimer fraction may be used, for example, as a raw material for the production of various chemicals, such as herbicides and pesticides. In other embodiments, the dimer may be fed to an alkylation reaction, where the dimer dissociates into constituent olefins and reacts with an alkane to produce an alkylate in the gasoline-boiling range. The dimer may also be hydrogenated to form gasoline-range hydrocarbons, such as octane, nonane, and other hydrocarbons. In yet other embodiments, the dimer containing stream may be used as a gasoline-range hydrocarbon blendstock without hydrogenation or alkylation.

The recovered heavy fraction, including the trimers, oxygenated oligomerization byproducts, and any other heavy components present, may be used as a blendstock for diesel fuel. The heavy fraction recovered according to embodiments disclosed herein may meet diesel fuel specifications, including being low in sulfur content and having a high flash point.

EXAMPLES

A process similar to that of FIG. 1 is used to produce dimers of isobutene. In addition to the separation components illustrated in FIG. 1, a methanol extraction column is also used, as well as a light oxygenate/$C_4$ splitter (i.e., dividing stream 108 of FIG. 1). A $C_4$ feed stream (102) including approximately 21.8 weight percent isobutene is fed to an oligomerization reactor at a feed rate of about 60,000 kg/h. Methanol (stream 104) is also fed to the reactor at a flow rate of about 75 kg/h. The resulting reactor effluent is then separated to recover oxygenates (stream 108), unreacted olefins (stream 108), a dimer fraction (stream 112), and a trimer/heavies fraction (stream 114).

The production of diisobutylene, including co-dimers dimethyl hexene and trimethylpentene, results in the product streams as detailed in Table 1. Due to the additional separation equipment and related feeds, the overall mass balance includes additional streams not listed in Table 1, however the streams presented provide sufficient details to indicate to one skilled in the art that processes according to embodiments disclosed herein may be used to recover a dimer product having a low amount of residual oxygenates, both lighter and heavier than the desired dimer product. As shown by the results listed in Table 1, processes disclosed according to embodiments disclosed herein may allow for the production and recovery of a dimer product having an oxygenate concentration of 400 ppm or less, by weight.

Embodiments disclosed herein may advantageously result in higher value end products. For example, hydrogenation of oxygenated hydrocarbons tends to saturate olefinic hydrocarbons, thus resulting in loss of octane value for gasoline blending and reduction of olefin yield available for alkylation. In contrast, embodiments disclosed herein do not chemically alter the composition of the selectively dimerized isobutene and, thus, does not diminish its value.

Yet another advantage of oligomerization processes according to embodiments disclosed herein is a higher yield of the overall fuel components. For example, in treating the selectively dimerized isobutene, the hydrogenation process breaks the oxygenates into lighter hydrocarbons and water, wherein the water is removed. Thus, the fuel value associated with the oxygen bonds in the oxygenates is wasted. In con-

TABLE 1

|  |  | Stream | | | | | |
| --- | --- | --- | --- | --- | --- | --- | --- |
|  |  | 102 | 104 | 112 | 114 | 108 - oxygenates | 108 - C4s |
| Mass Flow Rate | kg/h | 60003 | 75 | 12356 | 1855 | 1303 | 45035 |
| Temperature | C. | 40 | 50.8 | 40 | 40 | 40 | 40 |
| Pressure | kPa-g | 1750 | 1570 | 500 | 1000 | 500 | 700 |
| Components | wt. % |  |  |  |  |  |  |
| Methane | wt. % | 0.07 | 0 | 0 | 0 | 0 | 0.09 |
| Propane | wt. % | 0.06 | 0 | 0 | 0 | 0 | 0.08 |
| Isobutane | wt. % | 1.08 | 0 | 0 | 0 | 0 | 1.44 |
| Isobutene | wt. % | 21.83 | 0 | 0 | 0 | 0 | 0.09 |
| 1-butene | wt. % | 37.36 | 0 | 0 | 0 | 0.01 | 36.58 |
| 1,3-butadiene | wt. % |  |  |  |  |  |  |
| Cis-2-butene | wt. % | 24.09 | 0 | 0 | 0 | 0.04 | 35.89 |
| n-butane | wt. % | 7.71 | 0 | 0 | 0 | 0.04 | 15.35 |
| 3-methyl-1-butene | wt. % | 7.7 | 0 | 0 | 0 | 0.01 | 10.26 |
| 2-methyl-1-butene | wt. % | 0.1 | 0 | 0 | 0 | 0.14 | 0.08 |
| 2-methyl-2-butene | wt. % | 0 | 0 | 0 | 0 | 0.24 | 0 |
| Diisobutylene | wt. % | 0 | 0 | 71.06 | 0.94 | 1 | 0 |
| dimethyl hexene | wt. % | 0 | 0 | 10.23 | 0.77 | 0.47 | 0 |
| Trimethyl pentene | wt. % | 0 | 0 | 18.68 | 0.29 | 0 | 0 |
| Triisobutylene | wt. % | 0 | 0 | 0 | 90.64 | 0.12 | 0 |
| Quad-isobutylene | wt. % | 0 | 0 | 0 | 1.54 | 0 | 0 |
| C9 ether | wt. % | 0 | 0 | 0.03 | 5.82 | 0 | 0 |
| Water | wt. % | 0.01 | 0.02 | 0 | 0 | 0 | 0.05 |
| Methanol | wt. % | 0 | 99.55 | 0 | 0 | 0 | 0.01 |
| MSBE | wt. % | 0 | 0 | 0 | 0 | 75.35 | 0 |
| TAME | wt. % | 0 | 0 | 0.01 | 0 | 17.67 | 0 |
| TBA and SBA | wt. % | 0 | 0 | 0 | 0 | 0.76 | 0 |
| DME | wt. % | 0 | 0.44 | 0 | 0 | 4.13 | 0.09 |

As described above, embodiments disclosed herein relate to oligomerization of isoolefins. In some embodiments, the isoolefins may be fractionated to obtain a fraction containing isoolefin dimers having a low oxygen content. One advantage of processes disclosed herein is lower operating costs. Fractionation does not require the use of hydrogen, as does the typical hydrogenation of oxygenated byproducts, which may result in significant cost savings, especially for an operator that does not have an indigenous source of hydrogen available on site. In addition, fractionation does not require the use of hydrogenation catalyst, which may result in significant cost savings by negating catalyst regeneration or replacement costs.

trast, as above, fractionation does not chemically alter the oxygenates, thus preserving their fuel value to be used, for example, in diesel fuel.

Yet another advantage of processes disclosed herein is the potential capital costs savings available to a retrofit facility. For example, whereas hydrogenation may require an additional expensive reactor, the operator of a retrofit facility may simply re-commission a distillation tower from a different service to perform the required fractionations.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for oligomerizing isoolefins, the process comprising:
   feeding an isoolefin to an oligomerization reaction zone;
   feeding an oxygen-containing reaction moderator, comprising at least one of water, tertiary butyl alcohol or mixtures thereof, to the oligomerization reaction zone;
   concurrently in the oligomerization reaction zone:
   contacting the isoolefin with an oligomerization catalyst to convert at least a portion of the isoolefin to oligomers comprising dimers and trimers of the isoolefin;
   reacting a portion of the moderator with a portion of at least one of the isoolefin and the oligomers to form an oxygenated oligomerization byproduct, wherein the oxygenated oligomerization byproduct comprises a $C_8$-$C_{12}$ alcohol;
   recovering an effluent from the oligomerization reaction zone comprising the oligomers and the oxygenated oligomerization byproduct;
   fractionating at least a portion of the effluent to recover a fraction comprising the oxygenated oligomerization byproduct and the trimers and a fraction comprising the dimers; and
   blending at least a portion of the fraction comprising oxygenated oligomerization byproduct and trimers with additional hydrocarbons to form a diesel fuel.

2. The process of claim 1, wherein the effluent further comprises oxygen-containing moderator, the fractionating further comprising recovering a fraction comprising the oxygen-containing moderator.

3. The process according to claim 2, further comprising recycling at least a portion of the fraction comprising the oxygen-containing moderator to the oligomerization reaction zone.

4. The process according to claim 3, wherein the fraction comprising the oxygen-containing moderator further comprises unreacted isoolefin.

5. The process according to claim 1, wherein the oligomerization reaction zone comprises a catalytic distillation reaction zone, the concurrently further comprising:
   separating the oligomers and the oxygenated oligomerization byproduct from unreacted isoolefins by fractionation;
   recovering the unreacted isoolefins from the catalytic distillation reaction zone as an overheads fraction;
   recovering the oligomers and the oxygenated oligomerization byproduct from the catalytic distillation reaction zone as the oligomerization reaction zone effluent.

6. The process according to claim 5, further comprising recycling at least a portion of the overheads fraction to the catalytic distillation reaction zone as reflux.

7. The process of claim 1, wherein the isoolefin comprises at least one of propylene, isobutene, and isopentene.

8. The process of claim 1, wherein the isoolefin comprises isobutene.

9. The process of claim 1, further comprising at least one of alkylating at least a portion of the dimers, hydrogenating at least a portion of the dimers, and blending at least a portion of the dimers to form a gasoline-range hydrocarbon blendstock.

10. The process of claim 1, wherein the oligomerization reaction zone comprises at least one of a distillation column reactor, a divided wall distillation column reactor, a fixed bed reactor, a bubble column reactor, a slurry reactor equipped with or without a distillation column, pulsed flow reactor, a catalytic distillation column wherein slurry solid catalysts flow down the column, and combinations thereof.

11. A process for oligomerizing isobutene, the process comprising:
   feeding isobutene to an oligomerization reaction zone;
   feeding an oxygen-containing reaction moderator, comprising at least one of water, tertiary butyl alcohol or mixtures thereof, to the oligomerization reaction zone;
   concurrently in the oligomerization reaction zone:
   contacting the isobutene with an oligomerization catalyst to convert at least a portion of the isobutene to oligomers comprising dimers and trimers of isobutene;
   reacting a portion of the moderator with a portion of at least one of the isobutene and the oligomers to form an oxygenated oligomerization byproduct, wherein the oxygenated oligomerization byproduct comprises a $C_8$-$C_{12}$ alcohol;
   recovering an effluent from the oligomerization reaction zone comprising the oligomers and the oxygenated oligomerization byproduct;
   fractionating at least a portion of the effluent to recover a fraction comprising the oxygenated oligomerization byproduct and the trimers and a fraction comprising the isobutene dimers and blending at least a portion of the fraction comprising oxygenated oligomerization byproduct and trimers with additional hydrocarbons to form a diesel fuel.

12. The process of claim 11, wherein the effluent further comprises oxygen-containing moderator, the fractionating further comprising recovering a fraction comprising the oxygen-containing moderator.

13. The process according to claim 12, further comprising recycling at least a portion of the fraction comprising the oxygen-containing moderator to the oligomerization reaction zone.

14. The process according to claim 13, wherein the fraction comprising the oxygen-containing moderated further comprises unreacted isobutene.

15. The process according to claim 11, wherein the oligomerization reaction zone comprises a catalytic distillation reaction zone, the concurrently further comprising:
   separating the oligomers and the oxygenated oligomerization byproduct from unreacted isobutene by fractionation;
   recovering the unreacted isobutene from the catalytic distillation reaction zone as an overheads fraction;
   recovering the oligomers and the oxygenated oligomerization byproduct from the catalytic distillation reaction zone as the oligomerization reaction zone effluent.

16. The process according to claim 15, further comprising recycling at least a portion of the overheads fraction to the catalytic distillation reaction zone as reflux.

17. The process of claim 11, further comprising at least one of alkylating at least a portion of the dimers, hydrogenating at least a portion of the dimers, and blending at least a portion of the dimers to form a gasoline-range hydrocarbon blendstock.

18. The process of claim 11, wherein the oligomerization reaction zone comprises at least one of a distillation column reactor, a divided wall distillation column reactor, a fixed bed reactor, a bubble column reactor, a slurry reactor equipped with or without a distillation column, pulsed flow reactor, a catalytic distillation column wherein slurry solid catalysts flow down the column, and combinations thereof.

19. A process for oligomerizing isoolefins, the process comprising:

feeding a hydrocarbon mixture comprising an isoolefin to an oligomerization reaction zone comprising a catalytic distillation reaction zone;

feeding an oxygen-containing reaction moderator, comprising at least one of water, tertiary butyl alcohol or mixtures thereof, to the oligomerization reaction zone;

concurrently in the oligomerization reaction zone:
 contacting the isoolefin with an oligomerization catalyst to convert at least a portion of the isoolefin to oligomers comprising dimers and trimers of the isoolefin;
 reacting a portion of the moderator with a portion of at least one of the isoolefin and the oligomers to form an oxygenated oligomerization byproduct, wherein the oxygenated oligomerization byproduct comprises at least a $C_8$-$C_{12}$ alcohol;
 converting substantially all of the isoolefin to oligomers and oxygenated oligomerization byproducts;
 separating the oligomers and the oxygenated oligomerization byproduct from at least a portion of the hydrocarbon mixture by fractionation;

recovering the least a portion of the hydrocarbon mixture from the catalytic distillation reaction zone as an overheads fraction;

recovering the oligomers and the oxygenated oligomerization byproduct from the catalytic distillation reaction zone as a bottoms fraction;

fractionating at least a portion of the bottoms fraction to recover a fraction comprising the oxygenated oligomerization byproduct and the trimers and a fraction comprising the dimers.

20. The process of claim 19, wherein the isoolefin comprises at least one of propylene, isobutene, and isopentene.

21. The process of claim 19, wherein the mixed hydrocarbon comprises a C4, C5, or C4-C5 light naphtha cut.

* * * * *